United States Patent [19]

Wagner

[11] Patent Number: 4,562,192

[45] Date of Patent: Dec. 31, 1985

[54] 6-SUBSTITUTED-5-PHENYLTETRAZOLO[1,5-A][1,2,4]TRIAZOLE[1,5-C]PYRIMIDINES, AND PHARMACEUTICAL COMPOSITIONS CONTAINING THEM

[75] Inventor: Hans Wagner, Skokie, Ill.

[73] Assignee: G. D. Searle & Co., Skokie, Ill.

[21] Appl. No.: 576,700

[22] Filed: Feb. 3, 1984

[51] Int. Cl.[4] .................. A61K 31/505; C07D 487/04; C07D 487/14
[52] U.S. Cl. .................................... 514/258; 514/267; 544/251; 544/263
[58] Field of Search ................ 544/251, 263; 424/251; 514/258, 267

[56] References Cited

U.S. PATENT DOCUMENTS 3,412,094  11/1968  Rorig et al. ................ 544/323
4,405,780   9/1983  Wagner .................... 544/263
4,483,987  11/1984  Wagner et al. .............. 544/263

Primary Examiner—Donald G. Daus
Assistant Examiner—Diana G. Rivers
Attorney, Agent, or Firm—Steven M. Odre

[57] ABSTRACT

This disclosure relates to a class of novel 6-substituted-5-phenyltetrazolo[1,5-a][1,2,4]triazole [1,5-c]pyrimidines and to pharmaceutical compositions containing such compounds. The compounds and compositions disclosed are useful as renal vasodilators, diuretics and/or anti-hypertensive agents for the treatment of hypertensive disorders in humans.

15 Claims, No Drawings

6-SUBSTITUTED-5-PHENYLTETRAZOLO[1,5-A][1,2,4]TRIAZOLE[1,5-C]PYRIMIDINES, AND PHARMACEUTICAL COMPOSITIONS CONTAINING THEM

The present invention relates to a class of novel compounds comprising 6-substituted-5-phenyltetrazolo[1,5-a][1,2,4]triazole[1,5-c]pyrimidines. This invention further relates to pharmaceutical compositions containing such compounds and to the use of such compounds and compositions as renal vasodilators, diuretics and antihypertensive agents in the treatment of hypertensive disorders.

BACKGROUND OF THE INVENTION

U.S. Pat. No. 3,412,094 discloses a class of 5-alkyl-2-amino-4-azido-6-phenylpyrimidines and pharmacologically acceptable salts thereof which are useful as diuretics. U.S. Pat. No. 4,405,780 describes a class of 8-substituted-7-phenyl-1,2,4-triazolo[4,3-c]/[2,3-c]pyrimidines-5-amines and amides which are useful as diuretic agents.

SUMMARY OF THE INVENTION

The present invention relates to a class of novel compounds of the formula

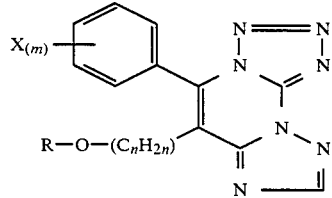

I wherein n is an integer of from 1 to 6; X is halo, $C_1$-$C_4$ alkoxy or $C_1$-$C_4$ alkyl; m is an integer of from 0 to 5; and R is hydrogen, $C_1$-$C_8$ alkyl, $C_2$-$C_8$ alkenyl, $C_2$-$C_8$ alkynyl, $C_1$-$C_8$ alkylsulfonyl, or a

group wherein $R^1$ is selected from the class consisting of $C_1$-$C_8$ alkyl, $C_2$-$C_8$ hydroxycarbonylalkyl, $C_1$-$C_8$ alkylamino, $C_3$-$C_{10}$ alkoxycarbonylalkylamino, adamantano, phenyl and substituted phenyl containing from 1 to 3 substituents selected from the class consisting of halo, $C_1$-$C_4$ alkyl and $C_1$-$C_4$ alkoxy; and azido tautomers thereof.

This invention further relates to pharmalogical compositions containing the compounds of formula (I) and to the use of such compounds and compositions as renal vasodilators, diuretics and anti-hypertensive agents in the treatment of hypertensive disorders.

Those skilled in the art will recognize that azido pyrimidines are disposed under favorable conditions to participate in a so called azido methine-tetrozole equilibrium. The compounds of formula (I) may exist in equilibrium as "tautomers" and may be represented in the tetrazolo form (A) or in the azido form (B) as indicated below:

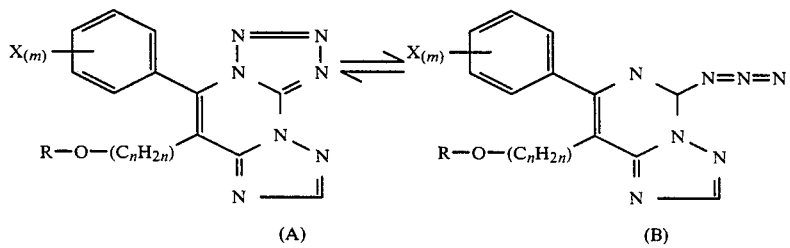

The relative amounts of the two tautomeric forms of the subject compounds in existence under any given circumstance are dependent upon the physical state of the involved substances and their environment—whether they are solid or liquid, and, if dissolved, in what solvent, at what temperature and at what pH. Because the various forms in which tautomers exist cannot readily be represented by a single formula, the subject compounds are hereinafter named and enformulated exclusively as tetrazoles *for convenience only;* both azido and tetrazolo forms, notwithstanding, are within the ambit of the described invention. It has been found that when the compounds of formula (I) are in a solid physical state, the compounds exist predominately in the azido form.

DETAILED DESCRIPTION OF THE INVENTION

The alkyl, alkenyl and alkynyl groups specified herein are straight chain or branched chain hydrocarbon moieties containing up to ten carbon atoms. Illustrative alkyl radicals include methyl, ethyl, propyl, isopropyl, butyl, isobutyl, sec-butyl, tert-butyl, pentyl, neopentyl, hexyl, isohexyl, heptyl, decyl and like monovalent, saturated acyclic, straight- or branched-chain, hydrocarbon groupings of the empirical formula

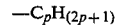

wherein p represents an integer of less than 9, and preferably less than 5. Representative alkenyl and alkynyl radicals are groups which can be thought of as derived from polycarbon alkyl radicals by displacement of two or more hydrogens to give rise to a double bond or a triple bond, respectively. Illustrative alkenyl radicals are vinyl, 1-propenyl, 2-propenyl, 1-methyl-1-propenyl, 2-methyl-1-propenyl, 1-butenyl, 2-butenyl, 3-butenyl, and the like. Illustrative alkynyl radicals are ethynyl, 1-propynyl, 2-propynyl, 1-butynyl, 2-butynyl, 3-butynyl, and the like.

The term "hydroxycarbonylalkyl" refers to radicals having the general structural formula

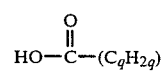

wherein q is an integer of less than 9. Representative of such radicals includes, but is not limited to, groups having the formula:

$$HO-\overset{O}{\underset{\|}{C}}-CH_2-, \quad HO-\overset{O}{\underset{\|}{C}}-(CH_2)_2-, \quad HO-\overset{O}{\underset{\|}{C}}-(CH_2)_7-,$$

$$HO-\overset{O}{\underset{\|}{C}}-\overset{CH_3}{\underset{|}{CH}}, \quad HO-\overset{O}{\underset{\|}{C}}-\overset{CH_3}{\underset{\underset{CH_3}{|}}{\overset{|}{C}}},$$

and the like.

The term "alkylamino" refers to radicals having the general structural formula $$(C_qH_{2q+1})-\overset{H}{\underset{|}{N}}-$$

wherein q is an integer of less than 9. Groups representative of such radicals includes, but is not limited to, methylamino, ethylamino, propylamino, isopropylamino, butylamino, octylamino and the like.

The term "alkoxycarbonylalkylamino" refers to radicals having the general structural formula $$(C_pH_{2p+1})-O-\overset{O}{\underset{\|}{C}}-(C_tH_{2t})-\overset{H}{\underset{|}{N}}-$$

wherein p and t are independently integers of less than 9. Representative of such radicals includes, but is not limited to groups having the formula:

$$CH_3-O-\overset{O}{\underset{\|}{C}}-(CH_2)_2-\overset{H}{\underset{|}{N}}-, \quad CH_3CH_2-O-\overset{O}{\underset{\|}{C}}-(CH_2)_3-\overset{H}{\underset{|}{N}}-,$$

$$CH_3CH_2-O-\overset{O}{\underset{\|}{C}}-CH_2-\overset{H}{\underset{|}{N}}-, \quad CH_3-O-\overset{O}{\underset{\|}{C}}-CH_2-\overset{H}{\underset{|}{N}}-,$$

$$CH_3-(CH_2)_6-O-\overset{O}{\underset{\|}{C}}-CH_2-\overset{H}{\underset{|}{N}}-,$$

and the like.

The term "halo" as used herein refers to fluoro, chloro, bromo, and iodo.

A preferred embodiment of the present invention comprises a class of compounds according to formula (I) wherein R is hydrogen, $C_1$-$C_8$ alkyl or a $$-\overset{O}{\underset{\|}{C}}-R^1$$

group. Another preferred embodiment of the present invention comprises a class of compounds according to formula (I) wherein n is an integer from 2 to 4, m is 0 and R is hydrogen, $C_1$-$C_8$ alkyl or a $$-\overset{O}{\underset{\|}{C}}-R^1$$

group wherein $R^1$ is $C_1$-$C_8$ alkylamino or $C_1$-$C_8$ alkyl. A more preferred embodiment of the present invention comprises a class of compounds according to formula (I) wherein n is 2, m is 0 and R is $C_1$-$C_8$ alkyl.

In addition it is preferred that m is an integer of from 0 to 3 and more preferably from 0 to 1.

The compounds of formula (I) wherein R is alkyl may be prepared in accordance with the following procedure:

An 8-(2-alkoxyalkyl)-7 phenyl-1,2,4-triazolo[2,3-c]pyrimidin-5-amine of formula (II):

II wherein $R^2$ is alkyl and n is an integer of from 1 to 6; is reacted with hydrochloric or hydrobromic acid in the presence of sodium nitrite to yield a 5-chloro or 5-bromo-8-(2-alkoxyalkyl)-7-phenyl[1,2,4]triazolo[1,5-c]pyrimidine of the formula (III)

III wherein $R^2$ and n are defined above and Y is cloro or bromo. A compound of formula (III) is then reacted with sodium azide in the presence of a suitable polar aprotic solvent such as for example dimethylsulfoxide or dimethylformamide to yield the 8-alkoxyalkyl-5azido-7-phenyltrazole[2,3-c]pyrimidines of the formula

IV wherein $R^2$ and n are above defined.

The compounds of formula (I) wherein R is hydrogen may be prepared by reacting, under non-aqueous conditions, a compound of formula (III) dissolved in trichloromethane, with boron trichloride in dichloromethane to yield a 5-chloro-or 5-bromo-7-phenyl[1,2,4]-triazolo[1,5-c]pyrimidine-8-alkanol of formula (V)

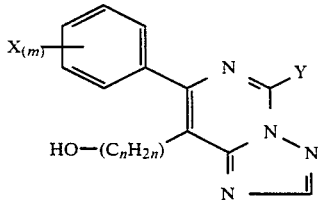

A compound of formula (V) is then reacted with sodium azide in the presence of a suitable polar aprotic solvent such as, for example, dimethylsulfoxide or dimethylformamide, to yield a 5-phenyltetrazolo[1,5-a][1,2,4]triazolo[1,5-c]pyrimidine-6-alkanol of formula (VI)

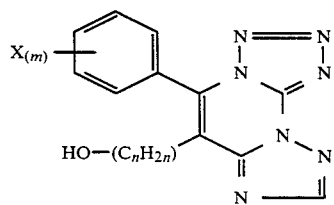

The compounds of formula (I) wherein R is a

group wherein $R^3$ is alkyl, carboxyalkyl, adamantano, phenyl or substituted phenyl may be prepared by reacting a compound of formula (VI) with a carbonyl halide of the formula

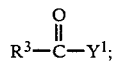

wherein $Y^1$ is fluoro, chloro, bromo or iodo; in the presence of a non-aqueous basic solvent such as pyridine.

The compounds of formula (I) wherein $R^1$ is alkylamino or alkoxycarbonylalkylamino may be prepared by reacting a compound of formula (VI) with an isocyanate of the formula

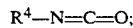

wherein $R^4$ is alkyl or alkoxycarbonylalkyl; in the presence of a non-aqueous solvent such as dichloromethane.

The compounds of the present invention may be administered by any suitable route, preferably in the form of a pharmaceutical composition adapted to such route, and in a dose effective for the treatment intended.

Accordingly, the invention provides a class of novel pharmaceutical compositions comprising one or more compounds of the present invention in association with one or more non-toxic, pharmaceutically acceptable carriers and/or diluents and/or adjuvants and if desired other active ingredients. The composition may for example be administered orally or by injection.

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules. These may with advantage contain an amount of active ingredient from about 5 to 250 mg preferably from about 25 to 150 mg. A suitable daily dose for a mammal may vary widely depending on the condition of the patient and other factors. However, a dose of from about 0.1 to 300 mg/kg body weight, particularly from about 1 to 100 mg/kg body weight may be appropriate.

The active ingredient may also be administered by injection as a composition wherein, for example, saline, dextrose or water may be used as a suitable carrier. A suitable daily dose is from about 0.1 to 100 mg per kg body weight injected per day in multiple doses depending on the disease being treated. A preferred daily dose would be from about 1 to 30 mg/kg body weight.

As indicated, the dose administered and the treatment regimen will be dependent, for example, on the disease, the severity thereof, on the patient being treated and his response to treatment and therefore may be widely varied.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et al., Remington's Pharmaceutical Sciences, 14th ed., Merck Publishing Co., Eaton, Pa., 1965.

Appropriate dosages, in any given instance, of course depend upon the nature and severity of the condition treated, the route of administration, and the species of mammal involved, including its size and any individual idiosyncrasies.

The following examples are intended to further illustrate the present invention and not to limit the invention in spirit or scope. In the examples, all parts are parts by weight unless otherwise expressly set forth.

EXAMPLE 1

A solution containing 100.8 g of 8-(2-ethoxyethyl)-7-phenyl[1,2,4]triazolo[1,5-c]pyrimidin-5-amine (0.36 moles) dissolved in 600 ml of concentrated hydrochloric acid and 420 ml. of water is cooled to 3° C. with constant stirring. To the cooled solution is added (below the surface of the solution) a mixture containing 54 g. of sodium nitrite (0.72 moles) in 75 ml of water over a period of fifteen minutes. The reaction mixture is stopped and stirred in an ice-bath for 0.5 hour and then stirred at room temperature for one hour. To the reaction mixture is added 150 ml of water and the resulting mixture is allowed to remain overnight at room temperature. A precipitate formed and the mixture is filtered and the precipitate is washed with water and dried yielding a crude product. The crude product is recrystallized from diethylether yielding 5-chloro-8-(2-ethoxyethyl)-7-phenyl[1,2,4]triazolo[1,5-c]pyrimidine represented by the structural formula

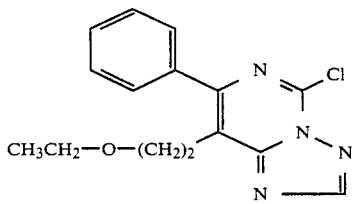

as a white solid having a melting point of 134°–135° C. and the following elemental analysis:

For $C_{15}H_{15}N_4ClO$: Calculated: C, 59.50; H, 4.99; N, 18.50; Cl, 11.71. Found: C, 59.33; H, 4.88; N, 18.34; Cl, 11.56.

EXAMPLE II

Employing the procedure of Example I but utilizing aqueous hydrobromic acid in lieu of hydrochloric acid yields 5-bromo-8-(2-ethoxyethyl)-7-phenyl[1,2,4]triazolo[1,5-c]pyrimidine represented by the structural formula

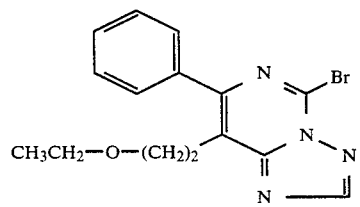

as a white solid having a melting point of 159°–160° C. and the following elemental analysis:

For $C_{15}H_{15}N_4BrO$: Calculated: C, 51.89; H, 4.35; N. 16.14; Br, 23.01. Found: C, 51.50; H, 4.23; N, 15.52; Br, 23.78.

EXAMPLE III

To a solution containing 30.2 g of 5-chloro-8-(2-ethoxyethyl)-7-phenyl[1,2,4]triazolo[1,5-c]pyrimidine (0.1 moles) dissolved in 200 ml of dimethylsulfoxide is added 20 g of sodium azide (0.3 moles). The resulting reaction mixture is heated to 65°–70° C. and then stirred for 5 hours. The reaction mixture is then stirred overnight at room temperature. The reaction mixture is then stirred into 1 liter of water and a precipitate forms. The mixture is filtered and the precipitate is washed with water and dried yielding a crude product. The crude product is chromatographed on silica gel and recrystallized from diethylether to yield 6-(2-ethoxyethyl)-5-phenyltetrazolo[1,5-a][1,2,4]triazolo[1,5-c]pyrimidine having the structural formula

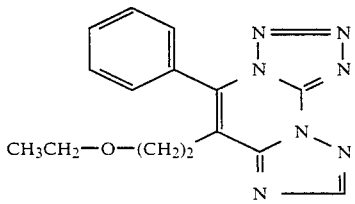

and the azido tautomer thereof as a white solid having a melting point of 114° C. and the following elemental analysis:

For $C_{15}H_{15}N_7O$: Calculated: C, 58.24; H, 4.89; N, 31.70. Found: C, 58.05; H, 4.83; N, 31.70.

EXAMPLE IV

Under non-aqueous conditions 200 ml of a mixture of boron trichloride (0.2 mol) and methylene chloride (1 mol) is added over a period of 20 minutes with vigorous stirring to a solution containing 30 g of 5-chloro-8-(2-ethoxyethyl)-7-phenyl[1,2,4]triazolo[1,5-c]pyrimidine (0.1 moles) dissolved in 300 ml of chloroform. The resulting reaction mixture is stirred at room temperature for 3 hours. To the reaction mixture is added 400 ml of water and the resulting mixture is stirred for 1.5 hours and then allowed to stand at room temperature. The aqueous and organic layers are separated and the organic layer is dried over sodium sulfate, filtered and evaporated yielding a residue. The residue is chromatographed on silica gel and recrystallized from diethyl ether to yield 5-chloro-7-phenyl[1,2,4]triazolo[1,5-c]pyrimidine-8-ethanol having the structural formula

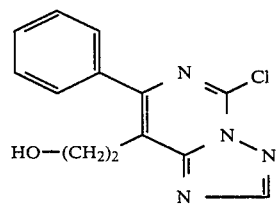

and the azido tautomer thereof as a white solid having a melting point of 104°–105° C. and the following elemental analysis:

For $C_{13}H_{11}ClN_4O$: Calculated: C, 56.83; H, 4.04; N, 20.40; Cl, 12.91. Found: C, 56.73; H, 3.98; N, 20.46; Cl, 12.81.

EXAMPLE V

To a solution containing 27.4 g of 5-chloro-7-phenyl[1,2,4]triazolo[1,5-c]pyrimidine-8-ethanol (0.1 mole) dissolved in 250 ml of dimethylsulfoxide is added 13 g of sodium azide (0.2 mole). The resulting reaction mixture is stirred for 5 hours at a temperature of 65°–70° C. and then stirred overnight at room temperature. The reaction mixture is poured in water with stirring. A precipitate forms and the mixture is filtered and the precipitate is washed with water and dried yielding a crude product. The crude product is recrystallized from diethyl ether to yield 5-phenyltetrazolo[1,5-a][1,2,4]triazolo[1,5-c]pyrimidine-6-ethanol having the structural formula

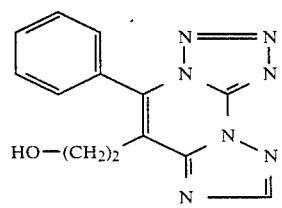

and the azido tautomer thereof as a white solid having a melting point of 110° C. and the following elemental analysis:

For $C_{13}H_{11}N_7O$: Calculated: C, 55.51; H, 3.94; N, 34.66. Found: C, 55.26; H, 3.80; N, 35.00.

EXAMPLE VI

To a solution containing 2.8 g of 5-phenyltetrazolo[1,5-a][1,2,4]triazolo[1,5-c]pyrimidine-6-ethanol (0.01 mole) dissolved in 15 ml of pyridine is added 1.5 ml of acetic anhydride (0.015 mole). The reaction mixture is maintained at room temperature for 48 hours and then is evaporated to dryness yielding a crude product. The crude product is chromatographed on silica gel and recrystallized from diethyl ether to yield 5-phenyltetrazolo[1,5-a][1,2,4]triazolo[1,5-c]pyrimidine-6-ethanol, acetate (ester) having the structural formula

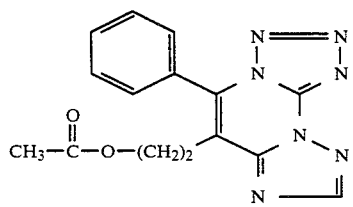

and the azido tautomer thereof as a white solid having a melting point of 114° C. and the following elemental analysis:

$C_{15}H_{13}N_7O_2$: Calculated: C, 55.72; H, 4.05; N, 30.33. Found: C, 55.92; H, 4.14; N, 29.93.

EXAMPLE VII

To a solution containing 1.4 g of 5-phenyltetrazolo[1,5-a][1,2,4]triazolo[1,5-c]pyrimidine-6-ethanol (0.005 mile) dissolved in 10 ml of pyridine is added, with stirring, 0.5 g of succinic anhydride. The reaction mixture is maintained at room temperature for 12 hours and then evaporated to dryness yielding a residue. The residue is taken up in methylene chloride, extracted with dilute hydrochloric acid, dried over sodium sulfate, filtered and evaporated yielding a crude product. The crude product is chromatographed on silica gel to yield 2-(5-phenyltetrazolo[1,5-a][1,2,4]triazolo[1,5-c]pyrimidin-6-yl)ethylsuccinate having the structural formula

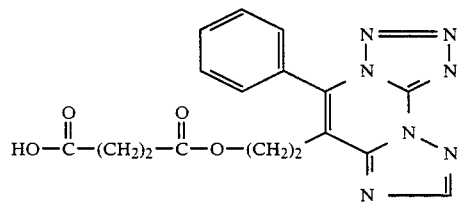

and the azido tautomer thereof as a white solid having a melting point of 144° C. and the following elemental analysis:

For $C_{17}H_{15}N_7O_4$: Calculated: C, 53.54; H, 3.96; N, 25.71. Found: C, 53.25; H, 3.94; N, 25.55.

EXAMPLE VIII

To a solution containing 1.4 g of 5-phenyltetrazolo[1,5-a][1,2,4]triazolo[1,5-c]pyrimidine-6-ethanol (0.005 mole) dissolved in 12 ml of pyridine is added 1.0 g of 1-adamantanecarbonyl chloride (0.005 mole). The reaction mixture is stirred for one hour and then allowed to stand overnight at room temperature. The reaction mixture is evaporated to dryness yielding a residue. The residue is taken up in methylene chloride, extracted with water, dried over sodium sulfate and evaporated to dryness yielding a crude product. The crude product is chromatographed on silica gel to yield 2-(5-phenyltetrazolo[1,5-a][1,2,4]triazolo[1,5-c]pyrimidin-6-yl)ethyl tricyclo[3.3.1.1$^{3,7}$]decane-1-carboxylate having the structural formula

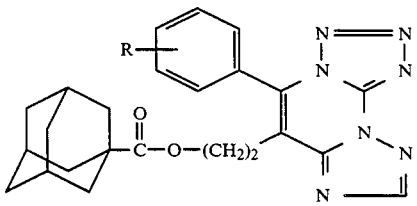

and the azido tautomer thereof as a white solid having a melting point of 129°–130° C. and the following elemental analysis:

$C_{24}H_{25}N_7O_2$: Calculated: C, 65.00; H, 5.68; N, 22.11. Found: C, 65.09; H, 5.676; N, 22.03.

EXAMPLE IX

To a solution containing 1.6 g of 5-phenyltetrazolo[1,5-a][1,2,4]triazolo[1,5-c]pyrimidine-6-ethanol (0.005 mole) dissolved in 15 ml of pyridine is added 1.3 g of octanoylchloride (0.008 mole). The reaction mixture is stirred for one hour and then allowed to stand overnight at room temperature. The reaction mixture is evaporated to dryness yielding a residue. The residue is taken up in methylene chloride, extracted with water, dried over sodium sulfate and evaporated to dryness to yield a crude product. The crude product is chromatographed on silica gel to yield 2-(5-phenyltetrazolo[1,5-a][1,2,4]triazolo[1,5-c]pyrimidin-6-yl) ethyloctanoate having the structural formula

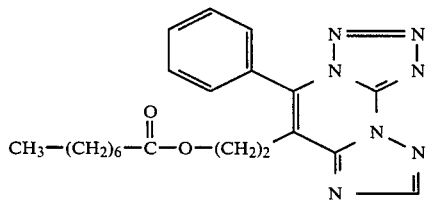

and the azido tautomer thereof as a viscous oil.

EXAMPLE X

To a solution containing 2.8 g of 5-phenyltetrazolo[1,5-a][1,2,4]triazolo[1,5-c]pyrimidine-6-ethanol (0.01 mole) dissolved in 20 ml of pyridine is added 2.1 g of 2,4-dichlorobenzoylchloride (0.01 mole). The reaction mixture is stirred for one hour and then allowed to stand overnight at room temperature. The reaction mixture is evaporated to dryness yielding a residue. The residue is taken up in methylene chloride, extracted with water, dried over sodium sulfate and evaporated to dryness to yield a crude product. The crude product is chromatographed on silica gel to yield 2-(5-phenyltetrazolo[1,5-l][1,2,4]triazolo[1,5-c]pyrimidin-6-yl)ethyl-2,4-dichlorobenzoate having the structural formula

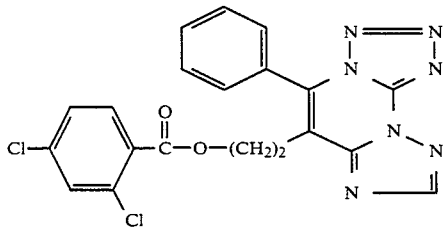

and the azido tautomer thereof as a white solid having a melting point of 124° C. and the following elemental analysis:

For $C_{20}H_{13}Cl_2N_7O_2$: Calculated: C, 52.88; H, 2.88; N, 21,58; Cl, 15.61. Found: C, 52.85; H, 2.97; N, 21.52; Cl, 15.29.

EXAMPLE XI

A mixture containing 2.8 g of 5-phenyltetrazolo[1,5-a][1,2,4]triazolo[1,5-c]pyrimidine-6-ethanol (0.01 mole), 5.7 ml of methylisocyanate, 1 drop pyridine in 50 ml of methylene chloride is refluxed for 7 hours. The reaction mixture is evaporated to dryness yielding a residue. The residue is chromatographed on silica gel yielding 5-phenyltetrazolo[1,5-a][1,2,4]triazolo[1,5-c]pyrimidine-6-ethanol, methylcarbamate ester having the structural formula

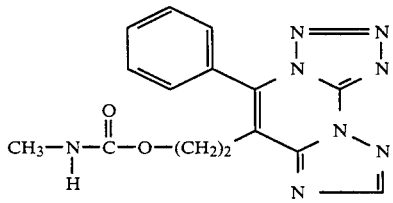

and the azido tautomer thereof as a white solid having a melting point of 161°-162° C. and the following elemental analysis:

For $C_{15}H_{14}N_8O_2$: Calculated: C, 53.25; H, 4.17; N, 33.12. Found: C, 53.72; H, 4.32; N, 31.87.

EXAMPLE XII

A mixture containing 2.8 g of N-[2-(5-phenyltetrazolo[1,5-a][1,2,4]triazolo[1,5-c]pyrimidin-6-yl)ethoxycarbonyl]glycine, ethyl ester (0.01 mole), 2.5 ml of ethylisocyanatocetate, 1 drop pyridine in 50 ml of chloroform is refluxed for 6 hours. The reaction mixture is evaporated to dryness yielding a residue. The residue is chromatographed on silica gel to yield N-[2-(5-phenyltetrazolo[1,5,a][1,2,4]triazolo[1,5-c]pyrimidin-6-yl)ethoxycarbonyl]glycine, ethyl ester, having the structural formula

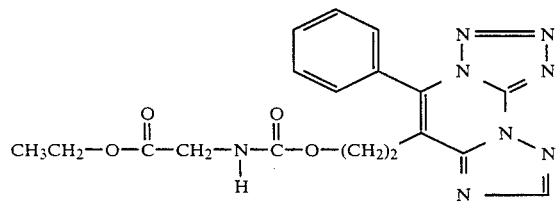

and the azido tautomer thereof, as a white solid having a melting point of 100°-101° C. and the following elemental analysis:

$C_{18}H_{18}N_8O_4$: Calculated: C, 52.68; H, 4.42; N, 27.30. Found: C, 52.60; H, 4.39; N, 27.32.

EXAMPLE XIII

A solution containing 2.8 g of 5-phenyltetrazolo[1,5-a][1,2,4]triazolo[1,5-c]pyrimidine-6-ethanol (0.01 mole) in 25 ml of pyridine is cooled in an ice-bath. To the cooled solution is dropwise added, with stirring, 1.2 ml of methanesulfonylchloride (0.015 mole). The resulting reaction mixture is stirred for 4 hours at room temperature. To the reaction mixture is added 1 ml of methanol and the resulting mixture is evaporated to dryness yielding a residue. The residue is chromatographed on silica gel to yield 5-phenyltetrazolo[1,5-a][1,2,4]triazolo[1,5-c]pyrimidine-6-ethanol, methanesulfonate ester having the structural formula

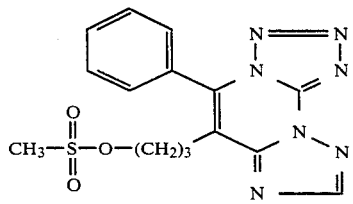

and the azido tautomer thereof, as a white solid having a melting point of 125°-126° C. and the following elemental analysis:

$C_{14}H_{13}N_7O_3S$: Calculated: C, 46.79; H, 3.65; N, 27.28; S, 8.92. Found: C, 47.12; H, 3.69; N, 27.04; S, 8.85.

Compounds of this invention are useful by virtue of their ability to function as renal vasodilators as indicated by the test in the following example.

EXAMPLE XIV

Adult mongrel female dogs are anesthetized with pentobarbital sodium (50 mg/kg i.p.). A short segment of the left renal artery is exposed by a flank incision and cleared of adhering tissue to accommodate positioning of an electromagnetic flowprobe (Carolina Medical Electronics, 8-10 mm inside diameter). The mean renal blood flow ("RBF") is measured by connecting the flowprobe to a flowmeter (Carolina Medical Electronics, model FM 501) and recorded on an oscillograph. The renal vascular resistance ("RVR") is calculated as the ratio of pressure/flow and expressed as millimeters of mercury per millileter per minute. The directly measured parameters, arterial blood pressure (milliliters of mercury) and RBF (milliliters per minute) are recorded on a multichannel oscillograph. Approximately 15 minutes are allowed to elapse after surgery for equilibrium of the preparation. Alterations in arterial blood pressure, RBF, RVR and urine flow resulting from application of various compounds of the present invention is determined in separate dogs. The compounds are applied intervenous, 3 mg/kg in 10% ethanol in 0.9% saline. A compound is rated active if it produces a 10% decrease in blood pressure, or a 20% increase in renal blood flow or a 50% increase in urine output.

Table I below, illustrates the activity of the preferred compounds of this invention. The results indicating arterial blood pressure, RBF and RVR are represented as the percent change from baseline and urine output is represented as the percent change in ml. collected before and after treatment.

TABLE I

| Compound of Example No. | Blood Pressure | RBF | RVR | Urine Output | Result |
|---|---|---|---|---|---|
| III | −19 | 56 | −49 | 447 | Active |
| V | −4 | 32 | −25 | 407 | Active |
| VI | −4 | 21 | −21 | 452 | Active |
| XI | −8 | 28 | −28 | 167 | Active |

The compounds of this invention are also useful by virtue of their ability to function as diuretics as indicated by the test in the following example.

EXAMPLE XV

To illustrate the diuretic properties of the compounds of the present invention, the compounds were assayed to determine the capacity of the compounds to increase urine volume as described by Lipschitz et al. [J. Pharmacol. Exp., Therap., 79 97 (1943)] and assigned potencies based upon paralled dose response curves in accordance with Finney [Statistical Method in Biological Assay, 2nd. ed., Charles Griffin & Company, Limited, London, 1964]. A compound is rated active if it produces a response which correlates to at least 10% of hydrochlorothiazide activity.

Table II illustrates the potencies of the preferred compounds of the present invention with respect to hydrochlorothiazide (i.e., % of hydrochlorothiazide activity). The typical dosage of hydrochlorothiazide as a diuretic for use in humans is 25 or 50 mg per oral administration.

TABLE II

| Compound of Example No. | % of hydrochlorothiazide activity | Result |
|---|---|---|
| III | 72 | Active |
| V | 303 | Active |
| VI | 150 | Active |
| XI | 21 | Active |

The compounds of this invention are also useful by virtue of their ability to function as anti-hypertensive agents as indicated by the test in the following example.

EXAMPLE XVI

A compound's ability to act as an antihypertensive agent is determined using spontaneous hypertensive rats (SHR). Male SHR are maintained in home for 1 or more weeks before use and are between 11 and 16 weeks old. The test compound is administered intravenously and the initial mean arterial blood pressure is measured directly via an arterial catheter implanted immediately before administration of the compound. Blood pressure readings are made 5, 10 and 15 minutes after administration of the compound. For each compound tested, the dosage is 10 mg/kg of body weight and is administered intravenously to unanesthetized, male, spontaneously hypertensive rats. A dose of test compound is rated active if the mean-post-treatment blood pressure of treated rats is significantly lower (P less than 0.05) than that of concurrent placebo controls. Statistical comparisons are made using the impaired student's test. Known compounds active in this as positive controls include guanethidine, apresoline, minoxidil, aldomet, clonidine and captopril.

Table III illustrates the activity of the preferred compounds of this invention.

TABLE III

| Compound of Example No. | Result |
|---|---|
| III | Active |
| V | Active |
| VI | Active |
| XI | Active |

Although this invention has been described with respect to specific modification, the details thereof are not to be construed as limitations, for it will be apparent that various equivalents, changes and modification may be resorted to without departing from the spirit and scope thereof and it is understood that such equivalent embodiments are intended to be included therein.

What is claimed is:

1. A compound of the formula

[chemical structure]

OR

[chemical structure]

wherein
n is an integer of from 1 to 6;
X is halo, $C_1$-$C_4$ alkyl, or $C_1$-$C_4$ alkoxy;
m is an integer of from 0 to 5;
R is hydrogen, $C_1$-$C_8$ alkyl, $C_2$-$C_8$ alkenyl, $C_2$-$C_8$ alkynyl, $C_1$-$C_8$ alkylsulfonyl or a $$-\overset{O}{\underset{\|}{C}}-R^1$$

group, wherein $R^1$ is selected from the class consisting of $C_1$-$C_8$ alkyl $C_2$-$C_8$ hydroxycarbonylalkyl, $C_1$-$C_8$ alkylamino, $C_3$-$C_{10}$ alkoxycarbonylalkylamino, adamantano, phenyl, substituted phenyl containing from 1 to 3 substituents selected from the class consisting of halo, $C_1$-$C_4$ alkyl and $C_1$-$C_4$ alkoxy.

2. A compound according to claim 1 wherein R is hydrogen, $C_1$-$C_8$ alkyl or a $$-\overset{O}{\underset{\|}{C}}-R^1$$

group wherein $R^1$ is $C_1$-$C_8$ alkyl or $C_1$-$C_8$ alkylamino.

3. A compound according to claim 2 wherein m is 0.

4. A compound according to claim 3 wherein R is $C_1$-$C_8$ alkyl.

5. A compound according to claim 4 wherein R is ethyl.

6. A compound according to claim 5 wherein n is 2.

7. A compound according to claim 3 wherein R is hydrogen.

8. A compound according to claim 7 wherein n is 2.

9. A compound according to claim 3 wherein R is a

group and $R^1$ is $C_1$-$C_8$ alkylamino.

10. A compound according to claim 9 wherein $R^1$ is a

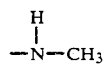

group.

11. A compound according to claim 10 wherein n is 2.

12. A compound according to claim 3 wherein R is a

group and $R^1$ is $C_1$-$C_8$ alkyl.

13. A compound according to claim 12 wherein $R_1$ is methyl.

14. A compound according to claim 13 wherein n is 2.

15. A pharmaceutical composition comprising a therapeutically effective amount of a compound of claim 1 and one or more non-toxic pharmaceutically acceptable carriers.

* * * * *